(12) United States Patent
Mäyrä-Mäkinen et al.

(10) Patent No.: US 8,309,073 B2
(45) Date of Patent: Nov. 13, 2012

(54) COMBINATION OF PROBIOTICS

(75) Inventors: Annika Mäyrä-Mäkinen, Helsinki (FI); Tarja Suomalainen, Helsinki (FI); Outi Vaarala, Helsinki (FI)

(73) Assignee: Valio Ltd., Helsinki (FI)

( * ) Notice: Subject to any disclaimer, the term of this patent is extended or adjusted under 35 U.S.C. 154(b) by 977 days.

(21) Appl. No.: 10/470,151

(22) PCT Filed: Jan. 17, 2002

(86) PCT No.: PCT/FI02/00035
§ 371 (c)(1),
(2), (4) Date: Oct. 22, 2003

(87) PCT Pub. No.: WO02/060276
PCT Pub. Date: Aug. 8, 2002

(65) Prior Publication Data
US 2004/0062758 A1    Apr. 1, 2004

(30) Foreign Application Priority Data
Jan. 25, 2001 (FI) .................... 20010157

(51) Int. Cl.
*A01N 63/00* (2006.01)
(52) U.S. Cl. .............. 424/93.3; 424/93.4; 424/93.45; 435/252.4
(58) Field of Classification Search .......... 435/252.4, 435/252, 9
See application file for complete search history.

(56) References Cited

U.S. PATENT DOCUMENTS

| | | | |
|---|---|---|---|
| 5,032,399 A | | 7/1991 | Gorbach et al. |
| 5,378,458 A | | 1/1995 | Mayra-Makinen et al. |
| 5,501,857 A | * | 3/1996 | Zimmer ................ 424/438 |
| 5,529,793 A | * | 6/1996 | Garner et al. ............ 426/61 |
| 5,895,648 A | | 4/1999 | Cavaliere Vesely et al. |
| 5,902,578 A | | 5/1999 | Halpin-Dohnalek et al. |

FOREIGN PATENT DOCUMENTS

| | | | |
|---|---|---|---|
| AU | 9928098 A | * | 7/1999 |
| EP | 0 904 784 A1 | | 3/1999 |
| EP | 1020123 A1 | | 7/2000 |
| FI | 92498 | | 8/1994 |
| WO | WO 97/29762 | | 8/1997 |
| WO | WO 97/29763 | | 8/1997 |
| WO | 97/34615 A1 | | 9/1997 |
| WO | WO 99/10476 | | 3/1999 |
| WO | WO 00/29007 | | 5/2000 |
| WO | WO 00/33854 | | 6/2000 |
| WO | 00/71138 A2 | | 11/2000 |

OTHER PUBLICATIONS

Mantere-Alhonen, S. Propionibacteria used as probiotics—a review. Lait. 1995. 75: 447-452.*
Fukushima, Y et al. Effect of a probiotic formula on intestinal immunoglobulin A production in healthy children. International Journal of Food Microbiology. 1998. 42: 39-44.*
Lait, vol. 79, 1999, Suomalainen et al; "Propionic Acid Bacteria as Protective Cultures in Fermented Milks and Breads"; pp. 165-174.
Clinical and Diagnositc Laboratory Immunology, vol. 6, No. 6, Nov. 1999, Kirjavainen et al; "Effects of Orally Administered Viable *Lactobacillus Rhamnosus* GG and *Propionibacterium Freudenreichii* Subsp. Shermanii JS on Mouse Lymphocyte Proliferation"; pp. 799-802.
Milchwissenschaft; "vol. 53, No. 11, 1998, Sarkar et al; "Process for the Manufacture of a New Modified Cultured Milk Product for Infants and Children; pp. 603-605.
Ouwehand et al, "Adhesion of probiotic micro-organisms to intestinal mucus", International Dairy Journal 9 (1999) 623-630.
Lehto et al, "Adhesion of Two *Lactobacilus* Strains, One *Lactococcus* and One *Propionibacterium* Strain . . . ", Bioscience Microflora vol. 16(1), 13-17, 1997.
Ling et al, "*Lactobacillus* Strain GG Supplementation Decreases Colonic Hydrolytic . . . ", 1994 American Institute of Nutrition; Manuscript received Apr. 5, 1993; Initial review completed May 4, 1993; Revision accepted Aug. 9, 1993.
Freeman, "Effects of Differing Purified Cellulose, Pectin, and Hemicellulose . . . ", Cancer Research 46, 5529-5532, Nov. 1986.
Adlercreutz et al, "Quantitative Determination of Lignans and Isoflavonoids . . . ", Scand J. Clin Lab Invest 1993:53 (Suppl 215):5-18.
Sanders et al, "Bringing a probiotic-containing functional food to the market: . . . ", Antonie van Leeuwenhoek 76:293-315, 1999.
Tannock, "Studies of the Intestinal Microflora: . . . ", Int. Dairy Journal 8, 1998, 527-533.
Mobley et al, "Microbial Ureases: Significance Regulation, and Molecular Characterization", Microbiological Reviews, Mar. 1989, p. 85-108.
Rowland, "Chapter 7 Toxicology of the Colon: Role of the Intestinal Microflora . . . ", Role in Nutrition Physiology and Pathology, G.R. Gibson and G.T. Macfarlane (eds.) pp. 155-174, CRC Press, Boca Raton, 1995.
Goldin, "Intestinal Microflora: Metabolism of Drugs and Carcinogens", Annals of Medicine 22: 43-48, 1990.
Ito et al, "Effects of Administration of Galactooligosaccharides on . . . ", Microbial Ecology in Health and Disease, vol. 3:285-292 (1990).
Lee et al, "The Coming of Age of Probiotics", Trends in Food Science & Technology, Jul. 1995 (vol. 6), pp. 241-245.
Fuller, "A Review Probiotics in man and animals", Journal of Applied Bacteriology, 1989, 66, 365-378.
Sako et al, "Recent Progress on Research and Applications of Non-Digestibles", International Dairy Journal, (1999) vol. 9, No. 1,, pp. 69-80.
Gallaher et al, "Probiotics, cecal microflora, and aberrant . . . ", Journal of Nutrition, (1996) vol. 126, No. 5, pp. 1362-1371.

(Continued)

*Primary Examiner* — Allison Ford
*Assistant Examiner* — Susan E Fernandez
(74) *Attorney, Agent, or Firm* — Nixon & Vanderhye P.C.

(57) ABSTRACT

The invention relates to a probiotic combination comprising different combinations of lactobacilli, propionic acid bacteria and/or bifidobacteria. The probiotics are preferably combined with a suitable prebiotic to form a synbiotic. The combination of the invention can be consumed as such or combined with a suitable foodstuff or pharmaceutical product, and it is therapeutically useful for example for stimulating the immune system and for general health improvement.

31 Claims, 2 Drawing Sheets

OTHER PUBLICATIONS

Gibson et al, "Dietary Modulation of the Human Colonic Micro biota: . . . ", J. Nutr. 125:1401-1412, 1995.

Cummings, Short-chain fatty acids in: Human Colonic Bacteria: Role in Nutrition Physiology and Pathology, G.R. Gibson and G.T. Macfarlane (eds.) pp. 101-130, CRC Press, Boca Raton, 1995.

Collado et al. "Protection mechanism of probiotic combination against human pathogens: In vitro adhesion to human intestinal mucus" Asia Pacific J. Clin Nutr. 15:570-575 (2006).

Ouwehand et al. "In vitro adhesion of propionic acid bacteria to human intestinal mucus" Lait 82:123-130 (2002).

Ouwehand et al. "The mucus binding of *Bifidobacterium lactis* Bb12 is enhanced in the presence of *Lactobacillus* GG and *Lact. delbrueckii subsp. bulgaricus*" Lett. Appl. Microbiol. 30:10-13 (2000).

Salminen et al. "Intestinal colonisation, microbiota and future probiotics?" Asia Pacific J. Clin. Nutr. 15:558-562 (2006).

Dougan et al. "CD1 expression on antigen-presenting cells" Curr. Top. Microbiol. Immunol. 314:113-141 (2007).

Husby et al. "Oral tolerance in humans. T cell but not B cell tolerance after antigen feeding" J. Immunol. 152:4663-4670 (1994).

Joint FAO/WHO Working Group "Guidelines for the evaluation of probiotics in food" London Ontario, Canada (Apr. 30 and May 1, 2002).

Lauw et al. "Of mice and man: TLR11 (finally) finds profilin" Trends Immunol. 26:509-511 (2005).

Pohjavuori et al. "*Lactobacillus* GG effect in increasing IFN-γ production in infants with cow's milk allergy" J. Allergy Clin. Immunol. 114:131-136 (2004).

Viljanen et al. "Probiotics in the treatment of atopic eczema/dermatitis syndrome in infants: A double-blind placebo-controlled trial" Allergy 60:494-500 (2005).

Kajander et al. "A probiotic mixture alleviates symptoms in irritable bowel syndrome patients: A controlled 6-month intervention" Alimentary Pharmacol. Ther. 22:387-394 (2005).

Kajander et al. "Clinical trial: Multispecies probiotic supplementation alleviates the symptoms of irritable bowel syndrome and stabilizes intestinal microbiota" Alimentary Pharmacol. Ther. 27:48-57 (2008).

Kekkonen et al. "Probiotic *Leuconostoc mesenteroides* ssp. *cremoris* and *Streptococcus thermophilus* induce IL-12 and IFN-γ production" World J. Gastroenterol. 14:1192-1203 (2008).

Myllyluoma et al. "Probiotic intervention decreases serum gastrin-17 in *Helicobacter pylori* infection" Digestive Liver Dis. 39:516-523 (2007).

Myllyluoma et al. "Probiotic supplementation improves tolerance to *Helicobacter pylori* eradication therapy—a placebo-controlled, double-blind randomized pilot study" Alimentary Pharmacol. Ther. 21:1263-1272 (2005).

Timmerman et al. "Monostrain, multistrain and multispecies probiotics—A comparison of functionality and efficacy" Int. J. Food Microbiol. 96:219-233 (2004).

Viljanen et al. "Probiotic effects on faecal inflammatory markers and on faecal IgA in food allergic atopic eczema/dermatitis syndrome infants" Pediatric Allergy Immunol. 16:65-71 (2005).

Viljanen et al. "Induction of inflammation as a possible mechanism of probiotic effect in atopic eczema-dermatitis syndrome" J. Allergy Clin. Immunol. 115:1254-1259 (2005).

Barlow et al. "Introduction of a qualified presumption of safety (QPS) approach for assessment of selected microorganisms referred to EFSA" EFSA J. 587:1-16 (2007).

Chr. Hansen Probiotics brochure (Apr. 2007), see BB-12® on second page.

Law ed., *Microbiology and Biochemistry of Cheese and Fermented Milk*, 2nd Ed., pp. 62-63, Springer (1997).

Ahlroos et al. "Quantitative strain-specific detection of *Lactobacillus rhamnosus* GG in human faecal samples by real-time PCR" J. Appl. Microbiol. 106:506-514 (2009).

Barrangou et al. "Comparison of the complete genome sequences of *Bifidobactrium animalis* subsp. *lactis*" J. Bacteriol. 191:4144-4151 (2009).

Guidelines for the Evaluation of Probiotics in Food: Report of a joint FAO/WHO Working Group meeting, London Ontario, Canada on Apr. 30-May 1, 2002.

Kajander et al. "Effects of multispecies probiotic supplementation on intestinal microbiota in irritable bowel syndrome" Aliment. Pharmacol. Ther. 26:463-473 (2007).

Kekkonen et al. "Probiotic leuconostoc mesenteroides ssp. *Cremoris* and *Streptococcus thermophilus* induce IL-12 and IFN-γ production" World J. Gastroent. 14:1192-1203 (2008).

Latvala et al. "Potentially probiotic bacteria induce efficient maturation but differential cytokine production in human monocyte-derived dendritic cells" World J. Gastroent. 14:5570-5583 (2008).

Masco et al. "Polyphasic taxonomic analysis of *Bifidobacterium animalis* and *Bifidobacterium lactis* reveals relatedness at the subspecies level: Reclassification of *Bifidobacterium animalis* as *Bifidobacterium animalis* subsp. *animalis* subsp. nov. and *Bifidobacterium lactis* as *Bifidobacterium animalis* subsp. *lactis*-subsp. nov." Int'l J. Systematic Evolutionary Microbiol. 54:1137-1143 (2004).

Matsuki et al. "Distribution of bifidobacterial species in human intestinal microflora examined with 16S rRNA-gene-targeted species-specific primers" Appl. Environ. Microbiol. 65:4506-4512 (1999).

Mayer et al. "Molecular discrimination of new isolates of *Bifidobacterium animalis subsp. lactis* from reference strains and commercial probiotic strains" Int'l Dairy Journal 17:565-573 (2007).

Myllyluoma et al. "Probiotic supplementation improves tolerance to helicobacter pylori eradication therapy—A placebo-controlled, double-blind randomized pilot study" Aliment. Pharmacol Ther. 21:1263-1272 (2005).

Olive et al. "Principles and applications of methods for DNA-based typing of microbial organisms" J. Clin. Microbiol. 37:1661-1669 (1999).

Reid "Probiotics and prebiotics—Progress and challenges" Int'l Dairy Journal 18:969-975 (2008).

Tynkkynen et al. "Comparison of ribotyping, randomly amplified polymorphic DNA analysis, and pulsed-field gel electrophoresis in typing of *Lactobacillus rhamnosus* and *L. casei* strains" Appl. Environ. Microbiol. 65:3908-3914 (1999).

Yeung et al. "Species-specific identification of commercial probiotic strains" J. Dairy Sci. 85:1039-1051 (2002).

Azaïs-Braesco et al. "Not all lactic acid bacteria are probiotics, . . . but some are" Br. J. Nutr. 103:1079-1081 (2010).

Bausserman & Michail "The use of *Lactobacillus* GG in irritable bowel syndrome in children: A double-blind randomized control trial" J. Pediatr. 147:197-201 (2005).

Besselink et al. "Probiotic prophylaxis in predicted severe acute pancreatitis: A randomised, double-blind, placebo-controlled trial" Lancet 371:651-659 (2008).

Christensen et al. "Immunomodulating potential of supplementation with probiotics: A dose-response study in healthy young adults" FEMS Immunol. Med. Microbiol. 47:380-390 (2006).

Commane et al. "Effects of fermentation products of pro and prebiotics on trans-epithelial electrical resistance in an in vitro model of the colon" Nutr. Cancer 51:102-109 (2005).

Drouault-Holowacz et al. "A double blind randomized controlled trial of a probiotic combination in 100 patients with irritable bowel syndrome" Gastroentérologie Clinique et Biologique 32:147-152 (2008).

Hol et al. "The acquisition of tolerance toward cow's milk through probiotic supplementation: A randomized, controlled trial" J. Allergy Clin. Immunol. 121:1448-1554 (2008).

Isolauri et al. "A human *Lactobacillus* strain (*Lactobacillus casei* sp. strain GG) promotes recovery from actue diarrhea in children" Pediatr. 88:90-97 (1991).

Isolauri et al. "Probiotics in the management of atopic eczema" Clin. Exp. Allergy 30:1604-1610 (2000).

Jain et al. "Influence of synbiotic containing *Lactobacillus acidophilus* La5, *Bifidobacterium lactis* Bb 12, *Steptococcus thermophilus, Lactobacillus bulgaricus* and oligofructose on gut barrier function and sepsis in critically ill patients: A randomised controlled trial" Clin. Nutr. 23:467-475 (2004).

Kaila et al. "Enhancement of the circulating antibody secreting cell response in human diarrhea by a human *Lactobacillus* train" Pediatr. Res. 32:141-144 (1992).

Kajander et al. "Clinical trial: Multispecies probiotic supplementation alleviates the symptoms of irritable bowel syndrome and stabilizes intestinal microbiota" Aliment. Pharmacol. Ther. 27:48-57 (2008).

Kajander et al. "A probiotic mixture alleviates symptoms in irritable bowel syndrome patients: A controlled 6-month intervention" Aliment. Pharmacol. Ther. 22:387-394 (2005).

Mantere-Alhdhen "Die propionibaktewien der molkereiindustrie als darmkanalmikroben" Finn. J. Dairy Sci. 40:1-95 (1982).

Myllyluoma et al. "Effects of multispecies probiotic combination on *Helicobacter pylori* infection in vitro" Clin. Vaccine Immunol. 15:1472-1482 (2008).

O'Sullivan & O'Morain "Bacterial supplementation in the irritable bowel syndrome. A randomised double-blind placebo-controlled crossover study" Digest. Liver Dis. 32:294-301 (2000).

Schiffrin et al. "Immunomodulation of human blood cells following the ingestion of lactic acid bacteria" J. Dairy Sci. 78:491-497 (1995).

Timmerman et al. "Design of a multispecies probiotic mixture to prevent infectious complications in critically ill patients" Clin. Nutr. 26:450-459 (2007).

Tsangalis et al. "Bioavailability of isoflavone phytoestrogens in postmenopausal women consuming soya milk fermented with probiotic bifidobacteria" Br. J. Nutr. 93:867-877 (2005).

Wildt et al. "Probiotic treatment of collagenous colitis: A randomized, double-blind, placebo-controlled trial with *Lactobacillus acidophilus* and *Bifidobacterium animalis* subsp. *lactis*" Inflamm. Bowel Dis. 12:395-401 (2006).

\* cited by examiner

COMBINATION OF PROBIOTICS

This application is the U.S. national phase of PCT/FI02/00035 filed 17 Jan. 2002, which designated the US.

FIELD OF THE INVENTION

The invention relates to a combination of probiotics, the combination comprising lactobacilli, propionic acid bacteria and/or bifidobacteria in various combinations. The probiotics are preferably combined with a suitable prebiotic to produce a synbiotic. The combination of the invention may be consumed as such or combined with a suitable foodstuff, such as a dairy product or a drink, and it is therapeutically useful for example for stimulating the immune system and for general health improvement.

BACKGROUND OF THE INVENTION

Probiotics are live microbes which, when administered to man or animals, promote the well being of the host by improving the intestinal microbial balance (Fuller, R. Probiotics in man and animals, 1989, J. Appl. Microbiol. 66:365-378). The best-documented probiotics include *L. rhamnosus* LGG, *L. johnsonii* LAI, *L. casei* Shirota and *Bifidobacterium lactis* Bb12. In addition, a number of other probiotics have been described in the literature of the art (see for example M. E. Sanders & J. H. in't Veld 1999. Antonie van Leeuwenhoek 76:293-315, Kluwer Academic Publishers). The health-promoting effects of probiotics include the balancing and maintenance of intestinal flora, stimulation of the immune system and anti-carcinogenic activity. The useful effects of probiotics in human intestines are based on several factors caused by live bacterial cells, their cell structures and metabolic products. Probiotics are usually administered in nutrients or as capsules.

A bacterium may be referred to as a probiotic if it essentially meets the following requirements (Lee, Y-K and Salminen, S. 1995 The coming age of probiotics. Trend Food Sci Technol, 6:241-245): it remains viable in the demanding conditions prevailing in the digestive tract (low pH of the stomach, acids of the digestive system, etc.); attaches to the walls of the intestine; metabolizes in the intestine; is technologically applicable (endures processing); exhibits clinically tested and reported health effects; and is safe to consume.

Prebiotics are nondigestible food ingredients which promote the health of humans by selectively stimulating the growth and activity of one or some probiotic bacteria in the colon (Gibson, G. R. and Roberfroid, M. B. 1995. Dietary modulation of the human colonic microbiota—introducing a concept of prebiotics. J. Nutr. 125:1401-1412). A prebiotic is usually a nondigestible carbohydrate (oligo- or polysaccharide) or a sugar alcohol which is not degraded or absorbed in the upper digestive tract. Known prebiotics used in commercial products include inulin (fructo-oligosaccharide, or FOS) and transgalacto-oligosaccharides (GOS or TOS).

A synbiotic is defined as a combination of a prebiotic and a probiotic, the prebiotic promoting the viability of the added microbe and its attachment to the intestine, thereby promoting health (Gibson and Roberfroid 1995, supra). When nondigestible carbohydrates that have passed through the small intestine are fermented in the colon, short-chain fatty acids, other organic acids, alcohols, hydrogen and carbon dioxide, for example, are formed (Gibson and Roberfroid 1995, supra). The primary fatty acids produced in fermentation are acetic acid, butyric acid and propionic acid (Cummings, J. H. Short-chain fatty acids, in: Human Colonic Bacteria: Role in Nutrition, Physiology and Pathology, G. R. Gibson and G. T. Macfarlane (eds.), pp. 101-130, CRC Press, Boca Raton, 1995). An increase in the number of short-chain fatty acids would be generally advantageous. Nondigestible carbohydrates are the principal substrate for colonic microbes, although they also may include compounds the intestinal fermentation of which is disadvantageous (Gibson and Roberfroid, 1995, supra).

Human digestive tract accommodates a plural number of bacteria which live in symbiosis with the host. There are great differences in microbial content between the different parts of the tract, about 95% of all the intestinal bacteria appearing in the colon, which is the most important part of the intestines. Over 400 bacterial species have been estimated to thrive in the colon. In addition to these, the intestines contain microbes known as transient microbes (G. R. Gibson and M. B. Roberfroid (eds.) Colonic Microbiota; Nutirition and Health. Kluwer Academic Publisher, Dordrecht, 1999). The dominating species are the following: *Bacteroides, Bifidobacterium, Coprococcus, Peptostreptococcus, Eubacterium* and *Ruminococcus*. The number of species *Lactobacillus, Streptococcus, Fusobacterium, Veillonella, Propionibacterium* and *Enterobacteriaceae* is slightly less. Some of the species represent useful microbes, whereas others may even be harmful. The average microbial content in feces is $10^{12}$ cfu/g (per dry matter). Bacteria degrade and ferment those food ingredients in the colon, which are not absorbed in the small intestine, the end products of the fermentation being absorbed in the intestine for use by the body. In addition to nutrition, the microbial balance of the colon is of major significance to the state of health of a man (Tannock, G. W. 1998. Studies of the intestinal microflora: A prerequisite for the development of probiotics, Int. Dairy J. 8:527-533). Changes in the composition of the intestinal flora or a sudden reduction in the amount of it (due to severe diarrhea, antibiotics treatment, etc.) increase the infectivity of potentially pathogenic species, which may have serious consequences (outbreak of allergies, intestinal diseases, cancer).

The $\beta$-glucuronidase enzymes produced by intestinal bacteria are assumed to contribute to the formation of carcinogenic compounds, for example. Steroids and other carcinogenic compounds metabolize in the liver and then conjugate with glucuronic acid. The bile delivers the conjugated glucurone compound to the small intestine and from there the compound passes further to the colon where the glucuronidase enzymens can hydrolyse the compound, thereby releasing toxic compounds into the colon (Rowland, I. R. 1995. Toxicology of the colon: role of the intestinal microflora, in: Human Colonic Bacteria, Role in nutrition, physiology, and pathology. Editors: Gibson, G. R. and Macfarlane, G. T., pp. 155-174, Boca Raton: CRC Press). It is assumed that species of *Eubacterium, Bacteroides* and *Clostridium* release greater amounts of these harmful enzymes into the intestines than representatives of species of *Bifidobacterium* and *Lactobacillus*. This would thus provide one reason why it would be advantageous that the intestinal flora is composed of bifidobacteria and lactobacilli.

In addition, glycosides originating from vegetables and tea, for example, are not absorbed in the small intestine and pass to the colon, where they may be hydrolysed by the action of $\beta$-glucosidases to form toxic or mutagenic aglycone compounds (Goldin, B. R. 1990. Intestinal Microflora: metabolism of drugs and carcinogens. Annals of Medicine 22:43-48).

Moreover, the intestinal flora produces urease enzyme which degrades urea into ammonia. High amounts of ammonia may be toxic to the epithel cells of the intestine (Mobley, H. L. T. and Hausinger, R. P. 1989. Microbial ureases: significance, regulation and molecular characterization. Microbiological Reviews 53:85-108).

Human intestinal flora is formed during the early years of life and no major changes take place in its composition thereafter. Only minor changes within the species may take place (in bifidobacteria, for example).

Along with the increased understanding of the importance of intestinal flora, research has thus been actively focused on discovering the factors that can be used to influence the composition of the flora and its operation (viability) in such a way that beneficial bacterial species would be strengthened and harmful ones reduced. It is assumed that the operation of microbes can be influenced by prebiotics that promote beneficial bacteria. Extensive research has been carried out into galactooligosaccharides (GOS) which are di-, tri-, tetra-, penta- and hexasaccharides and which primarily contain galactose units. They are prepared enzymatically from lactose and the content of the end product depends on the enzyme used (Matsumoto, K. et al. 1993. Galactooligosaccharides, in: Oligosaccharides. Production, properties and applications. Ed. Nakakuki, T., Japanese Technology Reviews. Vol. 3. No. 2., pp. 90-116, Gordon and Breach Science Publishers, Switzerland, Australia). GOS has earlier been demonstrated to exhibit for example bifidogenic properties, i.e. those promoting the growth of bifidobacteria (Ito, M. et al. 1990. Effect of administration of galactooligosaccharides on the human faecal microflora, stool weight, and abdominal sensation. Microb. Ecol Health Dis. 3:285-292).

DESCRIPTION OF THE BACKGROUND ART

Both products containing an individual probiotic strain and combinations of a plural number of different probiotics have been abundantly described in the literature of the art. Synbiotics have also been described in the literature of the art.

Publication EP 904 784, N. V. Nutricia, for example, describes a probiotic product containing *Bifidobacterium, Enterococcus faecium* and *Lactobacillus*. In addition, the product may contain prebiotics, such as polysaccharide or non-degradable starch, and immunoglobulines, vitamines, etc. According to the publication, the product has a health-promoting effect in that it stimulates the immune system, for example. The effect has not, however, been shown in clinical tests, neither has any other biological activity been studied.

WO 00/33854, N. V. Nutricia, describes a product comprising a probiotic and oligosaccharides. The probiotics particularly referred to are *Lactobacillus* and *Bifidobacterium*, although *Pediococcus, Propionibacterium, Leuconostoc* and *Saccharomyces* are also mentioned. The prebiotics involved include transgalactooligosaccharides (TOS) and fructooligosaccharides (FOS). According to the publication, a particularly advantageous combination comprises *Lactobacillus rhamnosus* and a transgalactooligosaccharide or a hydrolysis product of potato galactane, this combination and its preparation being also illustrated in the examples. According to the publication, the product has health-promoting effects and it is particularly useful in the treatment of intestinal disorders. However, its activity has not been demonstrated in any way.

WO 97/34615, University of New South Wales, describes a probiotic composition containing, in addition to one or more probiotics, resistent (non-degradable) starch and oligosaccharide, a synergistic effect being obtained between the three components. The probiotics mentioned are *Saccharomyces, Bifidobacterium, Bacteroides, Clostridium, Fusobacterium, Propionibacterium, Lactococcus, Streptococcus, Enterococcus, Staphylococcus, Peptostreptococcus* and *Lactobacillus*, and the oligosaccharides include, among many others, fructo- and galacto-oligosaccharides. The examples show the synergistic effect of bifidobacteria, maize starch and fructooligosaccharides on the amount of bifidobacteria. Any therapeutic effect, however, has not been described.

U.S. Pat. No. 5,895,648, Sitia-Yomo S.p.A., describes a probiotic composition comprising, in the form of lyophilized, live bacteria, at least two species of bifidobacteria and at least two species of lactobacilli or streptococcus combined with one or more oligosaccharides. The composition comprises altogether 4 to 20 parts by weight of probiotics and 5 to 22 parts by weight of oligosaccharides, of which for example galacto- and fructo-oligosaccharides, inuline in particular, are mentioned. The probiotics mentioned include *Bifidobacterium breve, Bifidobacterium infantis, Bifidobacterium longum, Bifidobacterium bifidum, Lactobacillus acidophilus, Lactobacillus bulgaricus, Lactobacillus casei, Lactobacillus plantarum, Streptococcus thermophilus* and *Streptococcus faecium*. According to the publication, a mixture containing probiotics and prebiotics can be added to milk-based desserts, milks or juices to balance the functioning of the intestine. Any biological activity of the combination has not, however, been described.

The publication Milchwissenschaft (1988) Vol. 53, No. 11, pp. 603 605, describes PAB-milk which comprises three bacterial strains: *Propionibacterium freudenreichii* subsp. *shermanii* MTCC 1371, *Lactobacillus acidophilus* R. and *Bifidobacterium bifidum* NDRI. Prebiotics have not been added to the product. According to the publication, PAB-milk is suitable for babies and children, also for those suffering from lactose intolerance.

WO 99/10476 describes the stimulating effect of specific bacterial strains, i.e. *Lactobacillus rhamnosus* HN001 (NM97/09514) and HN067 (NM97/01925), and *Lactobacillus acidophilus* HN017 (NM97/09515) and *Bifidobacterium lactis* HN019 (NM97/09513), on the immune system, measured as enhanced phagocytosis. The strains can be used individually, or added to dairy products or pharmaceutical preparations.

U.S. Pat. No. 5,902,578, Abbott Laboratories, relates to a method for preventing and treating diarrhea with a mixture of *Lactobacillus reuterii, Lactobacillus acidophilus* and *Bifidobacterium infantis*, the mixture being prepared as a powder, liquid or pills.

Biological and therapeutic effects of probiotics and synbiotics of the above type have also been described in the background art. As examples may be mentioned Gallagher, D. et al. Journal of Nutrition (1996) Vol. 126, No. 5, pp. 1362-1371, which describes the effects of bifidobacteria and *Lactobacillus acidophilus* on colon cancer in rats and states that the best results were obtained by using both the bacteria and a fructooligosaccharide, and Kirjavainen, P. et al. Clinical and Diagnostic Laboratory Immunology (November 1999) Vol. 6, No. 6, pp. 799-802, which describes the positive effects of two, separately studied, lactic acid strains, *Lactobacillus rhamnosus* GG and *Propionibacterium freudenreichii* subsp. *shermanii* JS, on the lymphocyte levels, and thereby the immune response, of mice. The combination of these two bacteria has not been described or studied.

The combining of probiotics with other substances having therapeutic effects has also been described in the literature of the art. For example, WO 97/29762 and WO 97/29763, Procter & Gamble Company, describes the use of lactobacilli and bifidobacteria combined with galacto- or fructooligosaccharides together with a plant of the genus *Ericaceae*, or an extract thereof for the treatment of urinary tract infections and intestinal disorders, and WO 00/29007, Reddy, describes the combining of probiotics, such as *Lactococcus, Lactobacillus, Pediococcus, Streptococcus, Propionibacterium, Brevibacterium, Penicillium* and *Saccharomyces* with herb-based natural products and drug-like substances.

Although probiotics and synbiotics have been extensively studied, good and versatile commercial products are not available to any significant extent. Consequently, there is continued, evident need to offer the consumers new products having clearly demonstrated probiotic effects and produced in a form that allows them to be used as a convenient part or supplement, for example, of the every-day diet.

BRIEF DESCRIPTION OF THE INVENTION

It is therefore an object of the present invention to provide a new probiotic-containing product the probiotic effect of which has been clearly demonstrated, which is pleasant to use, and healthy for the consumer.

These objects were achieved with a new combination of the invention which comprises a plural number of probiotics. The present invention is thus based on a new combination comprising (2) lactobacilli strains, a propionic acid bacterium and/or a bifidobacterium. In addition, the combination preferably comprises a prebiotic supporting the growth of the abovementioned microbes.

According to the invention, two strains of lactobacilli are mainly used, i.e. *Lactobacillus rhamnosus* GG (ATCC 53103) and *Lactobacillus rhamnosus* LC705 (DSM 7061). The propionic acid bacterium is usually *Propionibacterium freudenreichii* ssp. *shermanii* JS (DSM 7067). The bifidobacterium may be any bifidobacterium having a probiotic effect, typically strains belonging to the species *Bifidobacterium breve, Bifidobacterium infantis, Bifidobacterium longum, Bifidobacterium bifidum* and *Bifidobacterium adolescentis* are used.

At least three of these bacteria are usually included, and the combination preferably includes *Lactobacillus rhamnosus* GG and/or *Propionibacterium freudenreichii* ssp. *shermanii* JS.

The most preferred combination is a mixture of four strains, *Lactobacillus rhamnosus* GG (ATCC 53103), *Lactobacillus rhamnosus* LC705 (DSM 7061), *Propionibacterium freudenreichii* ssp. *shermanii* JS (DSM 7067) and *Bifidobacterium infantis* Bbi99 (DSM 13692). However, any bifidobacterium (such as Bbl2) may be included in the combination, if desired. The prebiotic used is preferably galactooligosaccharide (GOS).

Another preferred composition is a combination of a bifidobacterium and a propionic acid bacterium, in which any bifidobacterium can be used together with *Propionibacterium freudenreichii* ssp. *shermanii* JS (DSM 7067).

The new combination can be used as such or as a part of another product, such as a pharmaceutical or a food product. The combination of the invention has an advantageous effect on the human intestinal balance in that it increases the enterolactone production and reduces a disadvantageously high pH value. The combination also influences the immune response by increasing the amount of lymphocytes and that of γ-interferon (IFN) and by reducing the formation of carcinogenic substances. The combination of the invention is thus useful for the prevention and treatment of intestinal disorders, allergies and cancer and for promoting general health.

In accordance with the present invention, the combination is thus also applicable as a therapeutic substance and in the preparation of therapeutic substances.

DETAILED DESCRIPTION OF THE INVENTION

Figure 1:
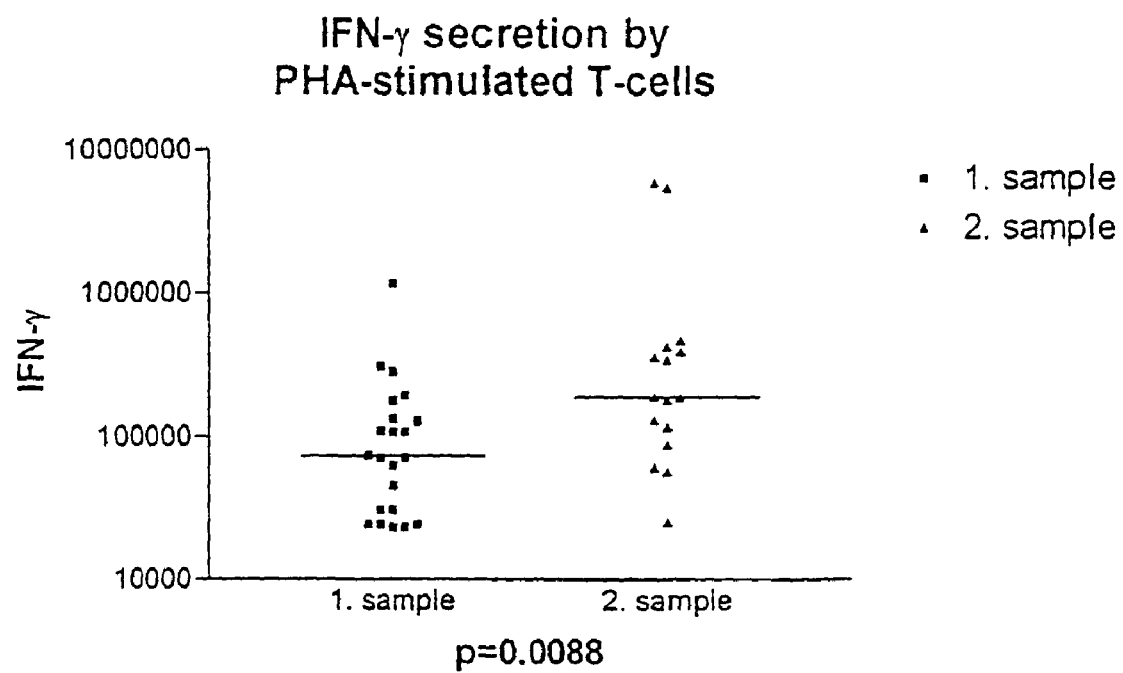
FIG. 1 shows IFN-γ secretion by PHA-stimulated T cells.

Of the strains used in the invention, *Lactobacillus rhamnosus* GG (LGG), *Lactobacillus casei* ssp. *rhamnosus* LC705 and *Propionibacterium freudenreichii* ssp. *shermanii* JS (PJS) have been described in the prior art. *Bifidobacterium infantis* Bbi99, which may be included in the combination, is a new strain and will be described in greater detail below.

*Lactobacillus rhamnosus* GG (LGG) is described for example in U.S. Pat. No. 5,032,399, Gorbach & Goldin. The strain is isolated from human feces, it is able to grow well in pH 3 and survives even lower pH values as well as high bile acid contents. The strain exhibits excellent adhesion to both mucus and epithelial cells. Lactic acid yield from glucose is good: when grown in MRS broth, the strain produces 1.5-2% of lactic acid. The strain does not ferment lactose and thus it does not produce lactic acid from lactose. The strain employs the following carbohydrates: D-arabinose, ribose, galactose, D-glucose, D-fructose, D-mannose, rhamnose, dulcitol, inositol, mannitol, sorbitol, N-acetylglucosamine, amygdalin, arbutin, esculin, salicin, cellobiose, maltose, saccharose, trehalose, melezitose, gentibiose, D-tagatose, L-fucose, and gluconate. The strain grows well at +15-45° C., the optimum temperature being 30-37° C. *Lactobacillus rhamnosus* GG is deposited with the depository authority American Type Culture Collection under accession number ATCC 53103.

*Lactobacillus casei* ssp. *rhamnosus* LC705 is described in greater detail in FI Patent 92498, Valio Oy. LC705 is a gram-positive short rod occurring in chains; it is homofermentative; weakly proteolytic; grows well at +15-45° C.; does not produce ammonia from arginine; is catalase-negative; when grown in MRS broth (LAB M), the strain produces 1.6% lactic acid having an optical activity of the L(+) configuration; the strain decomposes citrate (0.169%), thereby producing diacetyl and acetoin; the strain ferments at least the following carbohydrates (sugars, sugar alcohols): ribose, galactose, D-glucose, D-fructose, D-mannose, L-sorbose, rhamnose, mannitol, sorbitol, methyl-D-glucoside, N-acetylglucosamine, amygdalin, arbutin, esculin, salicin, cellobiose, maltose, lactose, sucrose, trehalose, melezitose, gentiobiose, D-turanose and D-tagatose. LC705 adheres weakly to mucus cells, but moderately to epithelial cells. The viability of the strain is good in low pH values and high bile acid contents. The strain survives well a salinity of 5% and fairly well a salinity of 10%. *Lactobacillus casei* ssp. *rhamnosus* LC705 is deposited with the Deutsche Sammlung von Mikroorganismen und Zellkulturen GmbH (DSM) under accession number DSM 7061.

*Propionibacterium freudenreichii* ssp. *shermanii* JS (PJS) is also described in greater detail in FI Patent 92498, Valio Oy. PJS is a gram-positive short rod; it ferments glucose, fructose, galactose and lactose; it ferments well lactate; and its optimum growth temperature is 32° C. The viability of the strain in low pH values and high bile acid contents is excellent. *Propionibacterium freudenreichii* ssp. *shermanii* JS is deposited with the Deutsche Sammlung von Mikroorganismen und Zellkulturen GmbH (DSM) under accession number DSM 7067.

*Bifidobacterium infantis* Bbi99 has been isolated from the feces of a healthy newborn. *B. infantis* Bbi99 is a gram-positive pleomorphic rod. The strain is catalase-negative, fructose-6-phosphate-phosphoketolase-positive (F6PPK) and both α- and β-galactosidase- and α- and β-glucosidase-positive. *B. infantis* Bbi ferments the following carbohydrates: ribose, galactose, D-glucose, D-fructose, D-mannose, methyl-D-mannose, N-acetylglucosamine, esculin, salicin, cellobiose, maltose, lactose, melibiose, and gentibiose. The optimum growth temperature is 30-40° C. and pH 6.5-7.0. When grown in broths comprising hexose, the strain produces L-lactic acid and acetic acid (in the ratio of 2:3). The G+C content of DNA is 55-67 mol %. *Bifidobacterium infantis* Bbi99 was deposited at the Deutsche Sammlung von Mikroorganismen und Zellkulturen GmbH (DSM), in accordance with the Budapest Treaty, under accession number DSM 13692 on 28 Aug. 2000.

The combination of the invention may also include other microorganisms, such as microorganisms and probiotics contained in starters used in the dairy industry. There are numeral well-documented strains of starters, which are commercially available from producers such as Hansen A/S, Denmark, and Danisco/Wiesby GmbH, Germany.

To prepare the combinations of the invention, the microorganisms are cultivated using processes conventional in the art. They can be cultivated as pure cultures or as different mixed cultures. The cultures can be used as such or they may be processed as desired for example by purifying, concentrating, lyophilising or finishing them to produce various preparations.

A sufficient amount of probiotics is used in the combination to produce the desired probiotic effect. The amount of each probiotic may thus vary within a broad range, depending on, for example, the strains used and their number, the total amount of cells of the probiotics, the total daily dose, and on other properties and ingredients of the product. A daily dose of the combination usually comprises about $10^6$-$10^{10}$ cfu of probiotics.

One or more prebiotics are preferably added to the combination to form a synbiotic. The prebiotic is selected according to the microorganisms included in the combination concerned such that it will support the growth of the microorganisms. Suitable prebiotics may include e.g. oligosaccharides, particularly galactooligosaccharide (GOS), palatinoseoligosaccharide, soybean oligosaccharide, gentiooligosaccharide, xylooligomers, non-degradable starch, lactosaccharose, lactulose, lactitol, maltitol, polydextrose, or the like. A sufficient amount of the prebiotic is added to the synbiotic to produce a prebiotic effect. What is a sufficient amount is determined for example according to the strain concerned, the amount of the prebiotics included and the other contents and the application of the product. The amount therefore also varies within a wide range; it may be from 0.5 to 5 g in a daily dose, for example.

The prebiotic does not necessarily need to be included in the combination. Depending on the end product and the purpose of use, it may be better to consume the prebiotic separately, although approximately at the same time with the probiotic combination. In some cases it may suffice to only consume the probiotic combination, the prebiotic being thus not needed at all. An example of this is a case where the intestinal conditions of the host are suitable for the growth of probiotics without an added prebiotic being needed, and when the prebiotic is contained in the normal diet (if it is consumed in porridge or rye bread, for example).

The present invention has shown that the microorganisms used meet the criteria set for probiotics: they survive well in the demanding conditions of the digestive tract, adhere well to intestinal cells and multiply well in the intestines. They have also been shown to exhibit excellent biological effects; for example, they increase the number of microorganisms desirable from the point of view of health and reduce the number of harmful microorganisms in the intestine, they reduce the activity of harmful enzymes and thereby the formation of harmful, or even carcinogenic, substances, and they have a stimulating effect on the immune response.

The combination of the invention can be used as such or in the form of capsules, pills or tablets, for example, manufactured in conventional processes of preparing pharmaceutical products. The combination of the invention may also be added to diverse edible products, such as foodstuffs, products of the beverage or confectionery industry, health-promoting products, natural products, etc. In the context of the present invention, products containing the combination of the invention, such as dairy products, particularly yogurts and other fermented milk products; cheeses and spreads; children's food; juices and soups; and capsules are preferred. A product in the form of a capsule usually only contains the probiotic combination, the prebiotic being consumed separately.

The end products are prepared in conventional processes, the combination being added either in connection with the preparation or thereafter, during the finishing of the end product.

The invention is described in greater detail with reference to the following examples, which are only intended to illustrate the invention and not to restrict its scope in any way.

EXAMPLE 1

Preparation of the Combination

The combination was prepared from a bacterial mixture, adding, when desired, galacto-oligosaccharide (GOS) as a prebiotic. The bacterial mixture was formed from bacterial cultures (concentrates or freeze-dried powders) of four strains, i.e. *Lactobacillus rhamnosus* GG (ATCC 53103), *Lactobacillus rhamnosus* LC705 (DSM 7061), *Propionibacterium freudenreichii* ssp. *shermanii* JS (DSM 7067) and *Bifidobacterium infantis* Bbi99 (DSM 13692).

Both LGG and *bifidobacterium* were cultivated individually.

LGG was cultivated in a medium comprising 5.0% of whey permeate (Valio Oy), 0.5% of casein hydrolysate (Valio Oy), 0.5% of technical yeast, and 0.0015% of $MnSO_4 \times H_2O$. The components of the medium were dissolved into water and the medium was sterilized (for 20 min at 120° C.). The cultivation was carried out at a temperature of 37° C. and a pH of 5.8 (adjusted with $NH_4OH$) for about 18 h and at a mixing rate of 100 rpm. After the cultivation the bacterial cells were concentrated, washed and freeze-dried using a 10% (v/v) protective agent supplement, such as a saccharose broth of 46%, or a similar alternative known to those skilled in the art. The final bacterial content was $>1\times10^9$ cfu/ml in the cultivation, $>1\times10^{10}$ cfu/g in the concentrate and $>1\times10^{11}$ cfu/g in the freeze-dried powder.

The composition of the growth medium of bifidobacteria was the following: whey permeate 4% (Valio Ltd.), casein hydrolysate 1.0% (Valio Ltd.), technical yeast extract 1.0% (LAB M), cystein-HCl 0.03% (Merck, Darmstadt, Germany). Other ingredients of the medium were first dissolved into water, then the cystein-HCl was added and the medium was sterilized (for 20 min at 120° C.). The cultivation was carried out in about 18-20 hours at a temperature of 37° C. and a pH of 6.7 (adjusted with $NH_4OH$) and at a mixing rate of 100 rpm. The bacterial content of the cultivation was $>1\times10^9$ cfu/ml. After the cultivation the bacteria cells were concentrated, washed and freeze-dried using a 10% (v/v) protective agent supplement, such as a saccharose broth of 46%, or a similar alternative known to those skilled in the art. The bacterial content in the concentrate was >1×10$^{10}$ cfu/g and in the freeze-dried powder >1×10$^{11}$ cfu/g.

LC705 and PJS were cultivated together by inoculating bacterial cells to a whey-based growth broth in a ratio of 1:2. The whey-based growth medium contained 3.5-5% of whey permeate (Valio Oy), 1.0% of caseinhydrolysate and 1.0% of yeast extract (Valio Oy). The strains were cultivated for three days at 30° C. with the pH maintained at 4.5 by means of an automated pH adjustment. After the cultivation, the content of each bacterial strain was >1×10$^9$ cfu/ml. After the cultivation the bacterial cells were concentrated, washed and freeze-dried using a 10% (v/v) protective agent supplement, such as a saccharose broth of 46% or a similar alternative known to a person skilled in the art. The content of each of the bacteria in the concentrate was >1×10$^{10}$ cfu/g and in the freeze-dried powder >1×10 cfu/g.

The strains may also be cultivated separately. In that case LC 705 is cultivated as described above in connection with the joint cultivation, only the cultivation time is 1 day at 30° C. PJS is cultivated in a whey-based growth medium comprising 2% of whey permentate, 1.0% of casein-hydrolysate and 1% of yeast extract. The strain is cultivated for 3 days at 30° C. in a pH value of 6.3, after which the process is carried out as above.

The concentrates or the powders are mixed in a ratio of 1:1:1. When LC705 and PJS have been cultivated separately, the mixing ratio is 1:1:1:1. The obtained mixture of concentrates or freeze-dried powders is used as a probiotic portion in the different product applications of the combination. The mixture is added to the product application to obtain the following final bacteria content in the product:

| | |
|---|---|
| LGG | >10$^6$ cfu/g of the product |
| LC705 | >10$^6$ cfu/g of the product |
| PJS | >10$^6$ cfu/g of the product |
| Bifidobacterium | >10$^6$ cfu/g of the product |

GOS (Valio Oy) was added, when desired, as a separate product to the product application to obtain a GOS concentration of about 0.5-5 g/dose in the product.

EXAMPLE 2

Adhesive Properties of the Strains and Their Tolerance in Intestinal Conditions

Adhesion of the probiotic strains to mucus was tested in accordance with Ouweland et al. (Ouwehand, A. C., Kirjavainen, P. V., Grönlund, M. -M., Isolauri, E., and Salminen, S. J. 1999. Adhesion of probiotic micro-organisms to intestinal mucus. Int. Dairy J. 9:623-630). LGG and probionic bacterium PJS adhered excellently to the intestinal mucus, Bbi99 moderately and LC705 weakly. Adhesion is a prerequisite for the microbe to produce beneficial effects in the intestines. On the other hand, LC705 is known to adhere well to epithet cells, similarly as LGG (Lehto, E. and Salminen S. 1997. Adhesion of two lactobacillus strains, one lactococcus strain and one propionibacterium strain to cultured human intestinal CaCO-2 cell lines. Bioscience Microflora 16: 13-17). This property is beneficial when there is an imbalance in the intestine and the protective mucus has been weakened.

TABLE 1

Adhesive properties of probiotic strains

| Strain | Adhesion % (+Std.) |
|---|---|
| LGG | 26.3 ± 1.3 |
| LC705 | 0.7 ± 0.2 |
| PJS | 24.9 ± 2.2 |
| Bbi99 | 4.6 ± 2.3 |

In vitro tests have shown the strains to endure physiological bile salt contents and the low pH of the stomach.

The strains were tested at different pH values in MRS broths the pH of which had been adjusted with lactic acid to values pH 4, pH 3 and pH 2. The strain to be studied (fresh culture) was inoculated into a pH broth of 1% and grown at 37° C. for 3 hours, after which the content of live cells was determined using an agar suitable for the strain (see Table 5). The strains maintained their viability in the 3-hour process in a pH value of 3 excellently. The propionic bacterium remained viable even in pH 2. In the test the bacteria were not protected by components carried by food (such as fat) and therefore they may be assumed to preserve even better when consumed in vivo together with food.

TABLE 2

Cell contents of strains cultivated in pH-adjusted MRS broths

| | Initial content cfu/ml | pH 4 cfu/ml | pH 3 cfu/ml | pH 2 cfu/ml |
|---|---|---|---|---|
| Bbi99 | 1 × 10$^7$ | 2 × 10$^7$ | <10 | <10 |
| PJS | 1 × 10$^8$ | 9 × 10$^7$ | 3 × 10$^7$ | 1 × 10$^4$ |
| LGG | 1 × 10$^7$ | 2 × 10$^7$ | 1 × 10$^7$ | <10$^2$ |
| LC705 | 6 × 10$^7$ | 2 × 10$^8$ | 4 × 10$^7$ | <10$^2$ |

With regard to bile salt tolerance, the strains were tested in MRS broths that contained 0.3% and 0.5% of Oxgal (Sigma) bile salt by inoculating 1% of the fresh culture into the bile salt MRS broth to be studied. The strains were cultivated in the broths for 3 hours at 37° C., after which the content of live cells was determined using an agar suitable for the strain (see Table 5). All strains survived the treatment excellently.

TABLE 3

Cell contents of strains cultivated in bile salt contents of 0.3% and 0.5%

| | Initial content (cfu/ml) | Bile salt 0.3% | Bile salt 0.5% |
|---|---|---|---|
| Bbi99 | 3 × 10$^7$ | 1 × 10$^7$ | 1 × 10$^7$ |
| PJS | 6 × 10$^7$ | 6 × 10$^7$ | 5 × 10$^7$ |
| LGG | 1 × 10$^7$ | 2 × 10$^7$ | 9 × 10$^6$ |
| LC705 | 1 × 10$^7$ | 2 × 10$^7$ | 1 × 10$^7$ |

EXAMPLE 3

Selecting a Prebiotic Suitable for the Combination

Alternative prebiotics were studied on individual strains by cultivating each strain in a sugar-free MRS broth to which was added 1% of the prebiotic to be studied. Each strain was cultivated for 1-2 days at its optimum temperature. Bacterial growth was observed during the test by determining the turbidity of the cultivation by spectrophotometry. As is shown in Table 4, best promoter for growth in all the four strains was a galacto-oligosaccharide (GOS) supplement of 1%.

TABLE 4

The effect of prebiotics on bacterial growth

| Prebiotic | LGG | LC705 | PJS | Bbi99 |
|---|---|---|---|---|
| GOS | ++ | ++ | ++ | + |
| FOS | − | − | − | − |
| Xylooligomers | + | ++ | + | + |
| Polydextrose | ++ | ++ | + | − |
| Arabinooligomers | − | − | − | − |
| Pectinoligomers | − | − | − | − |
| Xylitol | − | − | − | − |
| Maltitol | − | ++ | − | − |
| Lactitol | − | ++ | − | − |

EXAMPLE 4

Preparation of the End Product

A functional drink (in Finnish 'tehojuoma'; Valio Oy) was used as a base for preparing a juice (dosage 65 ml/day) to which was added 0.1 g of freeze-dried mixture of bacteria/dose (=65 ml) and 3.8 g of 70% GOS syrup/dose (=65 ml). Corresponding juice with no added GOS syrup or bacterial mixture was used as a control.

The bacterial contents of the finished juice were as follows:

| | |
|---|---|
| LGG | >$10^7$ cfu/ml |
| LC705 | >$10^7$ cfu/ml |
| PJS | >$10^8$ cfu/ml |
| Bbi99 | >$10^7$ cfu/ml |

The product was used in the following clinical tests in which pro=juice+probiotic supplement and syn=juice+probiotic+prebiotic supplement.

EXAMPLE 5

Clinical Effects of the Combination of the Invention

The drink described in example 4, which contained the above described probiotic combination (Pro) or the probiotic combination and a prebiotic (Syn), was clinically tested on 20 males. The test persons took the drink daily in accordance with the study plan and during the study they were not allowed to consume any other probiotic-containing product. The study scheme was such that the test started with a run-in period continued by a probiotics period of two weeks and a subsequent synbiotics period, and it ended with what is known as a wash-out period.

| The study scheme and schedule | | | | |
|---|---|---|---|---|
| week 8 \| 3 week | N (week 11) *\| 2 week | N (week 13) *\| 2 week | N (week 15) *\| 2 week | N (week 17) *\| |
| run-in without probiotic | pro | Syn | normal diet without probiotic | |

At the end of each period, the test persons gave a feces sample and a blood sample (=N).

Microbes and enzymes were analysed from the feces samples and enterolactone content and immune response from the blood.

5.1. Microbes
Amount of Microbes

The total lactic acid bacterial content, LGG, LC705, the total propionic acid bacterial content, PJS, and the total bifidobacteria content were determined applying methods known in the art and the parameters shown in Table 5.

TABLE 5

Methods for determining microbes

| Determination | Agar | Cultivation temperature/time | |
|---|---|---|---|
| Lactobacilli | MRS | 37° C./3 days | anaerobic |
| LGG | MRS + 0.005% vancomycin (Sigma) | 37° C./3 days | |
| LC705 | MRS + 0.005% Vancomycin | 37° C./3 days | |
| Propionic bacteria | Mod. YEL | 30° C./7 days | anaerobic |
| PJS | Mod. YEL | 30° C./7 days | anaerobic |
| Bifidobacteria | Raffinoseagar (RB) | 37° C./2 days | anaerobic |

Effect On the Intestinal Bacterial Cell Content in vivo

The contents of LGG, LC705 and PJS increased significantly in the samples of the test persons during the period they used the probiotic-containing product (Table 6). Since bifidobacteria contents were high from the very beginning of the test, changes have presumably only taken place within the species.

TABLE 6

Bacterial contents (log, cfu/g of fec s; ±std.)

| | Initial content cfu/g | After intake of probiotic, cfu/g | After intake of synbiotic, cfu/g | Wash-Out cfu/g |
|---|---|---|---|---|
| MHB (tot) | 6.0 (±1,2) | 6.1 (±1,2) | 6.1 (±1,0) | 4.5 (±1,6) |
| LGG | 2.3 (±1,0) | 4.7 (±1,7) | 5.3 (±1,2) | 3.0 (±1,6) |
| LC705 | 2.0 (±0) | 5.2 (±1,3) | 5.4 (±1,0) | 2.8 (±1,1) |
| Propion | 2.7 (±1,4) | 5.7 (±1,6) | 5.6 (±1,4) | 2.4 (±1,7) |
| Bifidobacteria | 8.2 (±1,5) | 8.6 (±2,1) | 8.8 (±2,2) | 8.3 (±2,1) |

Addition of synbiotic to the product consumed in the intake test improved the viability of the added probiotics in the intestine. This is shown by the increase in the LGG content during the synbiotics period, for example.

Effect on pH Value

The pH level of persons having an initial pH level of over 7 decreased in the groups that took the probiotic mixture and the synbiotic, whereas no decrease was observed in persons with an initial pH value lower than 7 (Table 7).

TABLE 7

Change in pH after probiotic and synbiotic supplement

| | Control | Probiotic alone | Synbiotic |
|---|---|---|---|
| pH > 7 | 7.2 | 6.9 | 6.7 |
| pH < 7 | 6.6 | 6.7 | 6.6 |

5.2. Enzymes

The feces samples were processed as described by Ling et al. (Ling, W-H., Korpela, R., Mykkänen, H., Salminen, S., and Hänninen, O. 1994 *Lactobacillus* GG supplementation decreases colonic hydrolytic and reductive activities in healthy female adults. Joumal of Nutrition 124, 18-24).

β-glucuronidase and β-glucosidase were determined as described by Freeman (Freeman, H. J. 1986. Effects of differing purified cellulose pectin, and hemicellulose fibre on faecal enzymes in 1,2-dimethyl-hydrazine-induced rat colon carcinogenesis. Cancer Research 46: 5529-5532) and urease according to the instructions of the manufacturer (Boehringer Mannheim cat. no. 542946).

During the test periods, there was a decrease in the contents of β-glucuronidase, urease and β-glucosidase during the probiotic intake and the synbiotic intake (Table 8). After the intake, the enzyme levels returned to normal. The synbiotic had a stronger decreasing effect on the enzyme levels than the probiotic mixture.

TABLE 8

Changes in enzyme contents (nmol/min/g of feces)

|  | Urease |  | Glucuronidase |  | Glucosidase |  |
| --- | --- | --- | --- | --- | --- | --- |
|  |  | Change % |  | Change % |  | Change % |
| Initial level | 1080 |  | 292 |  | 746 |  |
| Probiotic | 895 | −17 | 214 | −27 | 673 | −9, 8 |
| Synbiotic | 592 | −45 | 186 | −36 | 448 | −40 |
| Wash-Out | 980 |  | 227 |  | 640 |  |

Metabolism of glucosidase and glucuronidase produces carcinogenic compounds. The significant decrease in enzyme activity produced by the probiotic and synbiotic combinations of the invention clearly demonstrate a positive effect with regard to the decreasing of the formation of carcinogenic substances.

5.3 Enterolactone Content

Enterolactone content was determined using the method of Adlercreutz et al. (Adlercreutz, H., Fostis, T., Lampe, J., Wähälä, K., Mäkelä, T., Brunow, G. and Hase, T. 1993. Quantitative determination of lignans and isoflavonoids in plasma of omnivorous and vegetarian women by isotope dilution gas-chromatography mass-spectrometry. Scan J. Clin Lab Invest 53: 5-18.)

The enterolactone levels of test persons with an initial enterolactone level of <10 nmol/l increased significantly as a result of the synbiotic intake (to a level of 11.2).

No changes were observed during the test in the enterolactone levels of persons whose serum enterolactone level was normal (10<x>30) already at the beginning of the test. The results are shown in Table 9.

TABLE 9

Enteronelactone cont nts during the t st periods
(grouping on the basis of initial level)

|  | 10 < x < 30 nmol/l | <10 nmol/l |
| --- | --- | --- |
| Initial level | 24.4 | 3.2 |
| Probiotic | 19.8 | 2.6 |
| Synbiotic | 23.9 | 11.2 |

Enterolactone content has been shown to clearly correlate with the risk of getting cancer: the higher the content, the lower the risk. This result thus also shows the beneficial effect of the probiotic and synbiotic combinations of the invention to a decreased cancer risk.

5.4. Immunological Studies

Effects on Lymphocyte Function

Lymphocyte function was studied before the intake of the synbiotic product was started and after 4 weeks after the intake had been started.

The lymphocyte function was studied as follows:

Lymphocytes were isolated from peripheral blood using Ficoll gradient. The lymphocytes were stimulated with PHA mitogen (Sigma) in RPMI cultivation broth (National Public Health Institute; department of nutrient broths) which contained 5% of inactivated AB+ serum (Finnish Red Cross) and L-glutamine. After 48 hours, cell culture medium was collected for cytokine determination from four adjacent culture wells having a cell density of 200 000 cells per 200 µl of culture broth in the well, either with or without the mitogen. The cells were harvested after 16 hours from the adding of thymidine and the incorporation into DNA (cpm) of radioactive thymidine was measured. The contents of cytokines IL4, IL-5, TGF-β1 and IFN-γ were determined from the cell culture broths by using the ELISA method.

Figure 2:
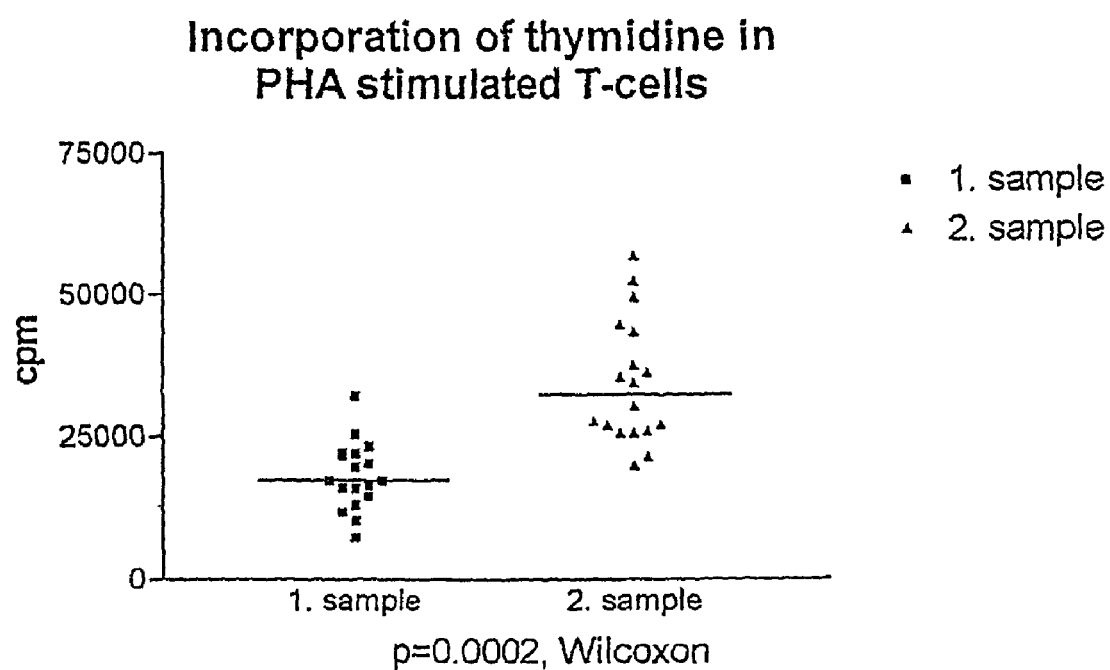
FIG. 2 shows incorporation of thymidine in PHA-stimulated T cells.

During the follow-up, no changes were detected in the IL4, IL-5 and TGF-β1 contents secreted by the lymphocytes. The IFN-γ content secreted by PHA-stimulated lymphocytes increased significantly during the follow-up (p=0.009, Wilcoxon test, see FIG. 1). Both spontaneous and PHA-stimulated proliferation of lymphocytes increased during the follow-up (p=0.0002 in both cases, Wilcoxon test, FIGS. 1 and 2).

According to the study results, the use of the synbiotic product thus enhances the proliferation of the lymphocytes and the secretion of IFN-γ cytokine of the test persons. IFN-γ belongs to what are known as Th1 cytokines, which strengthen cytotoxic lymphocyte function and are antagonists of IL4 and TGF-β1 cytokines. Low IFN-γ secretion has been reported for persons prone to allergies. In addition, children with a predisposition to atopy and allergy reactions have been presumed to suffer from slow maturing of IFN-γ secretion. The significant stimulating effect of the combinations of the invention on IFN-γ secretion thus proves their efficiency in the prevention and treatment of allergies.

The invention claimed is:

1. A composition of probiotics which consists of *Lactobacillus rhamnosus* GG (ATCC 53103), *Lactobacillus rhamnosus* LC705 (DSM 7061), *Propionibacterium freudenreichii* ssp. *shermanii* JS (DSM 7067) and a bifidobacterium, wherein the bifidobacterium is *Bifidobacterium infantis* Bbi99 (DSM 13692) or *Bifidobacterium lactis* Bb12, and the amount of probiotics in the composition is sufficient to produce a probiotic effect.

2. The composition of claim 1, wherein the bifidobacterium is *Bifidobacterium infantis* Bbi99 (DSM 13692).

3. The composition of claim 1, comprising from about $10^6$ colony forming units (cfu) to about $10^{10}$ cfu of each of the probiotics.

4. The composition of claim 1, wherein the bifidobacterium is *Bifidobacterium lactis* Bb12.

5. The composition of claim 1, wherein the amount of the probiotics in the composition is sufficient to reduce formation of carcinogenic or other harmful compounds.

6. A probiotic composition comprising only four probiotic strains *Lactobacillus rhamnosus* GG (ATCC 53103), *Lactobacillus rhamnosus* LC705 (DSM 7061), *Propionibacterium freudenreichii* ssp. *shermanii* JS (DSM 7067) and a bifidobacterium, wherein the bifidobacterium is *Bifidobacterium infantis* Bbi99 (DSM 13692) or *Bifidobacterium lactis* Bb12, in amounts sufficient to produce a probiotic effect; and at least starter microbes used in the dairy industry or a prebiotic.

7. The probiotic composition of claim 6 comprising both starter microbes and a prebiotic.

8. The probiotic composition of claim 6 comprising a prebiotic which is an oligosaccharide.

9. The probiotic composition of claim 8, wherein the oligosaccharide is a galacto-oligosaccharide.

10. The composition of claim 6, wherein the amount of the probiotic strains in the probiotic composition is sufficient to reduce formation of carcinogenic or other harmful compounds.

11. A probiotic composition comprising only four probiotic strains *Lactobacillus rhamnosus* GG (ATCC 53103), *Lactobacillus rhamnosus* LC705 (DSM 7061), *Propionibacterium freudenreichii* ssp. *shermanii* JS (DSM 7067) and a bifidobacterium, wherein the bifidobacterium is *Bifidobacterium infantis* Bbi99 (DSM 13692) or *Bifidobacterium lactis* Bb12, in amounts sufficient to produce a probiotic effect; and a prebiotic.

12. The composition of claim 11, wherein the amount of the probiotic strains in the probiotic composition is sufficient to reduce formation of carcinogenic or other harmful compounds.

13. A method of using the composition of claim 1 in preparing a product selected from the group consisting of foodstuff products, products of beverage or confectionary industry, health-promoting products and natural products.

14. The method of claim 13 further comprising using at least starter microbes or a prebiotic in preparing the product.

15. The method of claim 14, wherein starter microbes and a prebiotic are used to prepare the product.

16. The method of claim 13, wherein the product is a dairy product, drink, juice or children's food.

17. The method of claim 13, wherein the product is in single dose form.

18. The method of claim 17, wherein the single dose form is a capsule.

19. The method of claim 14, wherein the prebiotic is an oligosaccharide and is used to prepare the product.

20. The method of claim 19, wherein the oligosaccharide is a galacto-oligosaccharide.

21. A method of adding the composition of claim 1 to a product selected from the group consisting of foodstuff products, products of beverage or confectionary industry, health-promoting products and natural products.

22. The method of claim 21 further comprising adding at least starter microbes or a prebiotic to the product.

23. The method of claim 22, wherein starter microbes and a prebiotic are added to the product.

24. The method of claim 21, wherein the product is a dairy product, drink, juice or children's food.

25. The method of claim 21, wherein the product is in single dose form.

26. The method of claim 25, wherein the single dose form is a capsule.

27. The method of claim 22, wherein the prebiotic is an oligosaccharide and is added to the product.

28. The method of claim 27, wherein the oligosaccharide is a galacto-oligosaccharide.

29. A method of using the composition of claim 1 which is comprised of providing the composition to a human for consumption.

30. The method of claim 29, wherein the composition is provided as a dairy product, drink, juice, soup or children's food.

31. The method of claim 29, wherein the composition is provided as a capsule.

* * * * *